(12) United States Patent
Kleinemolen et al.

(10) Patent No.: US 11,944,735 B2
(45) Date of Patent: Apr. 2, 2024

(54) BLOOD PLASMA SEPARATION DEVICE

(71) Applicant: Truvian Sciences, Inc., San Diego, CA (US)

(72) Inventors: Ian Kleinemolen, San Diego, CA (US); Dena Marrinucci, San Diego, CA (US); Kameel Michael Abi-Samra, Carlsbad, CA (US)

(73) Assignee: Truvian Sciences, Inc., San Diego, CA (US)

( * ) Notice: Subject to any disclaimer, the term of this patent is extended or adjusted under 35 U.S.C. 154(b) by 0 days.

(21) Appl. No.: 18/130,635

(22) Filed: Apr. 4, 2023

(65) Prior Publication Data
US 2023/0241608 A1 Aug. 3, 2023

Related U.S. Application Data

(62) Division of application No. 16/515,974, filed on Jul. 18, 2019, now Pat. No. 11,638,918.

(Continued)

(51) Int. Cl.
*A61M 1/34* (2006.01)
*A61M 1/36* (2006.01)
(Continued)

(52) U.S. Cl.
CPC ........ *A61M 1/3496* (2013.01); *A61M 1/3693* (2013.01); *B01L 3/502* (2013.01);
(Continued)

(58) Field of Classification Search
CPC ............ G01N 33/491; G01N 33/5002; A61M 1/3496; A61M 1/3472; A61M 1/3693;
(Continued)

(56) References Cited

U.S. PATENT DOCUMENTS

| 9,108,198 B2 | 8/2015 | Kim et al. |
| 2004/0182795 A1 | 9/2004 | Dorian et al. |
| 2014/0341788 A1 | 11/2014 | Kim et al. |

FOREIGN PATENT DOCUMENTS

EP 2 559 991 A1 2/2013

OTHER PUBLICATIONS

International Search Report dated Oct. 15, 2019, regarding PCT/US2019/044018.

(Continued)

*Primary Examiner* — John Kim
(74) *Attorney, Agent, or Firm* — Snell & Wilmer, L.L.P.; April Wurster (57) ABSTRACT

A device for separating blood plasma from whole blood includes a first reservoir and a second reservoir. The first reservoir is configured to receive a sample of whole blood including red blood cells and includes a collection region and a constricted region. The second reservoir is fluidically connected to the constricted region of the first reservoir, such that, responsive to centrifugal force applied to the device, the sample of whole blood disposed within the first reservoir separates into a first fraction and a second fraction. The first fraction is located in the collection region and includes blood plasma from which substantially all red blood cells have been removed. The second fraction is located in the second reservoir and includes blood plasma and red blood cells that have been removed from the first fraction by the centrifugal force. The constricted region inhibits the second fraction from entering the collection region.

29 Claims, 9 Drawing Sheets

Related U.S. Application Data (60) Provisional application No. 62/722,050, filed on Aug. 23, 2018.

(51) Int. Cl.
  *B01L 3/00* (2006.01)
  *G01N 33/49* (2006.01)
  *G01N 33/50* (2006.01)

(52) U.S. Cl.
  CPC ..... *B01L 3/50273* (2013.01); *B01L 3/502746* (2013.01); *G01N 33/491* (2013.01); *G01N 33/5002* (2013.01); *A61M 1/3472* (2013.01); *B01L 2200/0621* (2013.01); *B01L 2300/0803* (2013.01); *B01L 2300/0816* (2013.01); *B01L 2300/0864* (2013.01); *B01L 2400/0409* (2013.01)

(58) Field of Classification Search
  CPC ............... B01L 3/50273; B01L 3/502; B01L 3/502746; B01L 2200/0621; B01L 2300/0803; B01L 2300/0816; B01L 2300/0864; B01L 2400/0409
  See application file for complete search history.

(56) References Cited

OTHER PUBLICATIONS

Li et al., "Out-of Plane Microvalves for Whole Blood Separations on Lab-on-a-CD," *J. Micromech. Microeng.* (2010), 20(10):105024, 10 pages, XP020198610.

Steigert et al., "Integrated Siphon-Based Metering and Sedimentation of Whole Blood on a Hydrophilic Lab-on-a-Disk," *Biomed. Microdevices* (2007), 9(5):675-679, XP019524286.

BLOOD PLASMA SEPARATION DEVICE

CROSS-REFERENCE TO RELATED APPLICATIONS

This application is a divisional application of U.S. application Ser. No. 16/515,974 filed Jul. 18, 2019, U.S. Pat. No. 11,638,918; which claims the benefit under 35 USC § 119(e) to U.S. Application Ser. No. 62/722,050 filed Aug. 23, 2018. The disclosure of each of the prior applications is considered part of and is incorporated by reference in the disclosure of this application.

BACKGROUND OF THE INVENTION

Field of the Invention

This application relates to separating blood plasma from whole blood.

Background Information

It can be useful to separate blood plasma from whole blood, for example to facilitate analysis of one or more components of the blood plasma.

SUMMARY OF THE INVENTION

Blood plasma separation devices, and methods of making and using the same, are provided herein.

A device for separating blood plasma from whole blood includes a first reservoir and a second reservoir. The first reservoir is configured to receive a sample of whole blood including red blood cells. The first reservoir includes a collection region and a constricted region. The second reservoir is fluidically connected to the constricted region of the first reservoir, such that, responsive to centrifugal force applied to the device, the sample of whole blood disposed within the first reservoir separates into a first fraction and a second fraction. The first fraction is located in the collection region and includes blood plasma from which substantially all red blood cells have been removed. The second fraction is located in the second reservoir and includes blood plasma and red blood cells that have been removed from the first fraction by the centrifugal force. The constricted region inhibits the second fraction from entering the collection region.

An outlet can be provided that is fluidically connected to the collection region. In addition, a channel can fluidically connect the outlet to the collection region. Such angle can be disposed at an acute angle relative to the collection region. The channel can be configured to substantially fill with the first fraction via capillary action responsive to termination of the centrifugal force.

The first reservoir can include a sample reservoir and a plasma reservoir fluidically connected to one another. With such arrangements, the sample reservoir can include an inlet configured to receive the sample of whole blood and the plasma reservoir can include the collection region and the constricted region. The sample reservoir, plasma reservoir, and second reservoir can each include one or more respective sidewalls and a respective lower surface. A cover (or other housing element) can be disposed over the sample reservoir, plasma reservoir, and second reservoir. The respective lower surface of the plasma reservoir can be closer to the cover than are the respective lower surfaces of the sample reservoir and the second reservoir. An upper surface of the sample of whole blood disposed within the sample reservoir can be further from the cover than is the lower surface of the plasma reservoir. The sample of whole blood disposed within the sample reservoir can flow upward toward the cover to contact the lower surface of the plasma reservoir responsive to the centrifugal force applied to the device.

In some variations, a first one of the sidewalls of the sample reservoir can be disposed at an angle (e.g., obtuse angle, etc.) angle relative to the lower surface of the sample reservoir. With such an arrangement, substantially all of the sample of whole blood disposed within the sample reservoir can flow upward along the first one of the sidewalls of the sample reservoir responsive to the centrifugal force applied to the device.

A portion of the sample of whole blood contacting the lower surface of the plasma reservoir can flow downward away from the cover to contact the lower surface of the second reservoir responsive to the centrifugal force applied to the device. The portion of the sample of whole blood contacting the lower surface of the plasma reservoir can flow downward along a first one of the sidewalls of the second reservoir responsive to the centrifugal force applied to the device.

The first and second fractions can each contact the cover after termination of the centrifugal force. The cover can be at least partially optically transparent. The cover can include a first aperture via which the sample reservoir receives the sample of whole blood and a second aperture via which the first fraction is withdrawn. The first aperture can be disposed over the sample reservoir. The second aperture can be disposed over the plasma reservoir. A channel can be provided that fluidically connects the outlet to the collection region, wherein the second aperture is located over the channel. The first and second apertures can each be configured to receive a pipette tip.

The cover can include a vent disposed over the sample reservoir.

The first fraction can substantially fill the plasma reservoir responsive to the centrifugal force.

The second fraction can substantially fill the second reservoir responsive to the centrifugal force.

The sample reservoir, the plasma reservoir, and the second reservoir can be arranged linearly with one another.

A meniscus of the first fraction can be disposed within the collection region.

In some variations, at least 75% of the red blood cells in the sample of whole blood are removed from the first fraction. In other variations, at least 99% of the red blood cells in the sample of whole blood are removed from the first fraction. In still other variations, 100% of the red blood cells in the sample of whole blood are removed from the first fraction.

The first reservoir can have varying volumes. For example, the first reservoir can have a volume about 25 µL to about 1 mL, or about 50-500 µL, or about 100-250 µL.

The second reservoir can have varying volumes. For example, the second reservoir can have a volume of about 20-80% of a volume of the first reservoir, or a volume of about 40-60% of a volume of the first reservoir.

A rotatable disc can be provided in which the first and second reservoirs are disposed.

In an interrelated aspect, blood plasma is separated from whole blood by receiving, by a first reservoir of a device, a sample of whole blood comprising red blood cells. The first reservoir includes a collection region and a constricted region. A centrifugal force is applied to the device to separate the sample of whole blood into a first fraction and a second fraction. The first fraction is located in the collection region and includes blood plasma from which substantially all red blood cells have been removed. The second fraction is located in a second reservoir of the device and includes blood plasma and red blood cells that have been removed from the first fraction by the centrifugal force. The constricted region inhibits the second fraction from entering the collection region.

DETAILED DESCRIPTION OF THE INVENTION

Blood plasma separation devices, and methods of making and using the same, are provided herein. The present blood plasma separation devices and methods suitably can be used to separate blood plasma from one or more other components of a sample of whole blood based on centrifugal forces. For example, the present blood plasma separation devices and methods can be used to separate blood plasma from blood cells within the sample of whole blood, so as to generate a fraction from which substantially all blood cells have been removed. Such fraction, which can primarily contain plasma, can collect within a first reservoir, and a fraction containing blood cells that have been removed can collect within a second reservoir. In some configurations provided herein, a constriction within the device inhibits blood cells from reentering the fraction that primarily contains plasma.

Figure 1A:
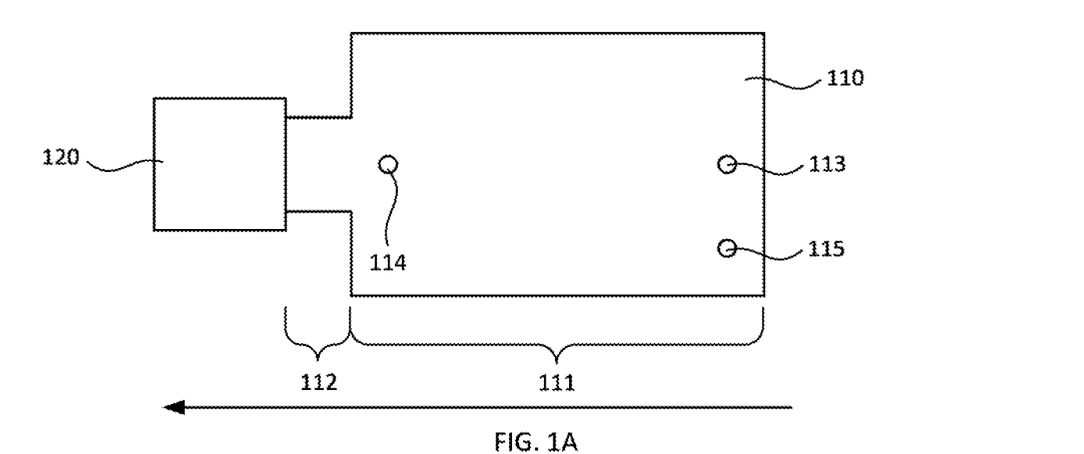
FIGS. 1A-1B respectively schematically illustrate plan and cross-sectional views of an exemplary blood plasma separation device, according to various configurations provided herein.
Figure 1B:
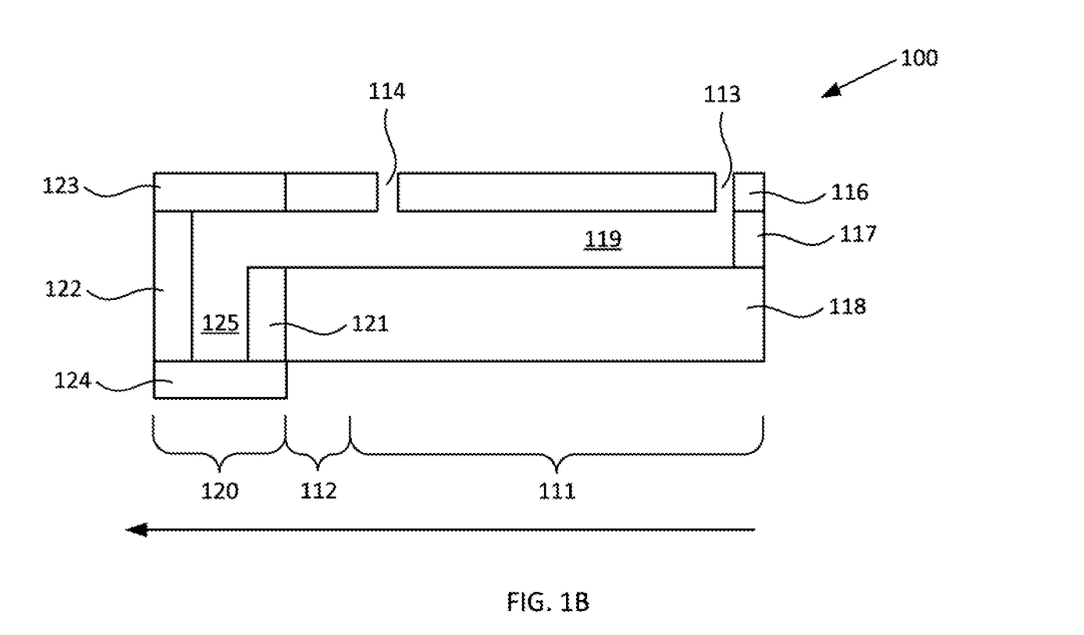

FIGS. 1A-1B respectively schematically illustrate plan and cross-sectional views of an exemplary blood plasma separation device, according to various configurations provided herein. Device 100 illustrated in FIGS. 1A-1B can include first reservoir 110 configured to receive a sample of whole blood comprising red blood cells. First reservoir 110 optionally can include collection region 111 and constricted region 112. Device 100 further can include second reservoir 120 that is fluidically connected to constricted region 112 of first reservoir 110. Optionally, first reservoir 110 and second reservoir 120 are arranged linearly with one another, and as a further option collection region 111, constricted region 112, and second reservoir 120 are arranged linearly with one another.

Optionally, device 100 includes inlet 113 via which first reservoir 110 can receive a sample of whole blood. Additionally, or alternatively, device 100 optionally includes outlet 114 via which a fraction primarily containing plasma can be withdrawn following centrifugation in a manner such as described herein with reference to FIGS. 1C-1D, 6, and 7A-7D. Additionally, or alternatively, device 100 optionally includes vent 115 via which air can escape from first reservoir 110 when a sample of whole blood is received within that reservoir, e.g., via optional inlet 113. Optionally, inlet 113, outlet 114, and/or vent 115 can be defined within cover 116, e.g., as optional first, second, and/or third apertures defined through cover 116, one or more of which apertures can be configured to receive a pipette tip.

First reservoir 110 and second reservoir 120 can have any suitable configuration and include any suitable number of upper surfaces (covers), lower surfaces (covers), and/or sidewalls which respectively can be discrete elements or can be integrally formed with one another, for example as described in greater detail herein with reference to FIGS. 2A-2D. In the nonlimiting configuration illustrated in FIG. 1B, first reservoir 110 includes upper surface (first cover) 116, sidewall(s) 117, and lower surface (second cover) 118 together providing an open area 119, and second reservoir 120 includes upper surface (third cover) 123, sidewall(s) 121, 122, and lower surface (fourth cover) 124 together providing an open area 125. It should be appreciated that terms such as "upper," "lower," "sidewall," and "cover" are not intended to be limiting of any particular orientation of the devices and methods provided herein, but instead to provide helpful terms by which various components optionally can be referred for the illustrated orientation and configuration. In the configuration illustrated in FIG. 1B, the lower surface 118 and cover 116 of first reservoir 110 are closer to one another than the lower surface 124 and cover 123 of second reservoir 120. One or more covers of device 100, e.g., one or more of upper surface 116, upper surface 123, lower surface 118, and/or lower surface 124 independently can be at least partially optically transparent.

Optional inlet port (first aperture) 113 can be disposed over a first region of open area 119, which is configured to receive a sample of whole blood and optionally can be considered to be a sample reservoir. Optional outlet port (second aperture 114) can be disposed over a second region of open area 119, which can be considered to be a plasma reservoir and is configured to collect a primarily plasma fraction which is generated responsive to centrifugal force in the direction indicated by the large arrow. It should be appreciated that a sample of whole blood can be introduced into open area 119 of collection region 111 via any suitable inlet, and is not limited to an aperture through a cover disposed over open area 119. For example, the sample of whole blood can be introduced into collection region 111 via a channel configured similarly to channel 330 described with reference to FIG. 3. It should also be appreciated that a fraction primarily containing blood plasma can be removed from open area 119 of collection region 111 via any suitable outlet, and is not limited to an aperture through a cover disposed over open area 119. For example, the fraction can be removed from collection region 111 via a channel configured similarly to channel 330 described with reference to FIG. 3. Such channel optionally can include an outlet configured similarly to outlet 314 described with reference to FIG. 3, or optionally can be connected to another device, for example configured to perform further processing of the fraction.

Figure 1C:
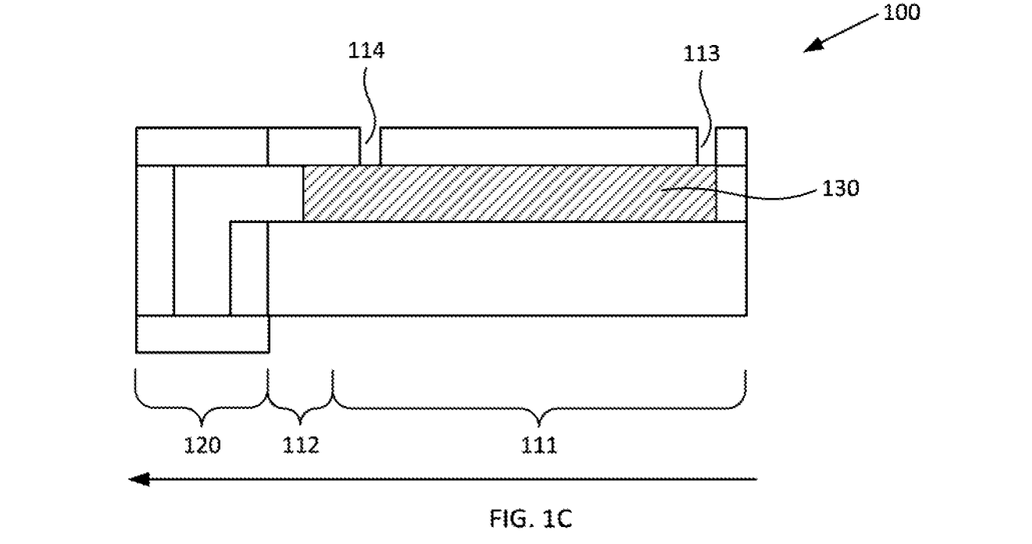
FIGS. 1C-1D schematically illustrates cross-sectional views of the exemplary blood plasma separation device of FIGS. 1A-1B during use, according to various configurations provided herein.
Figure 1D:
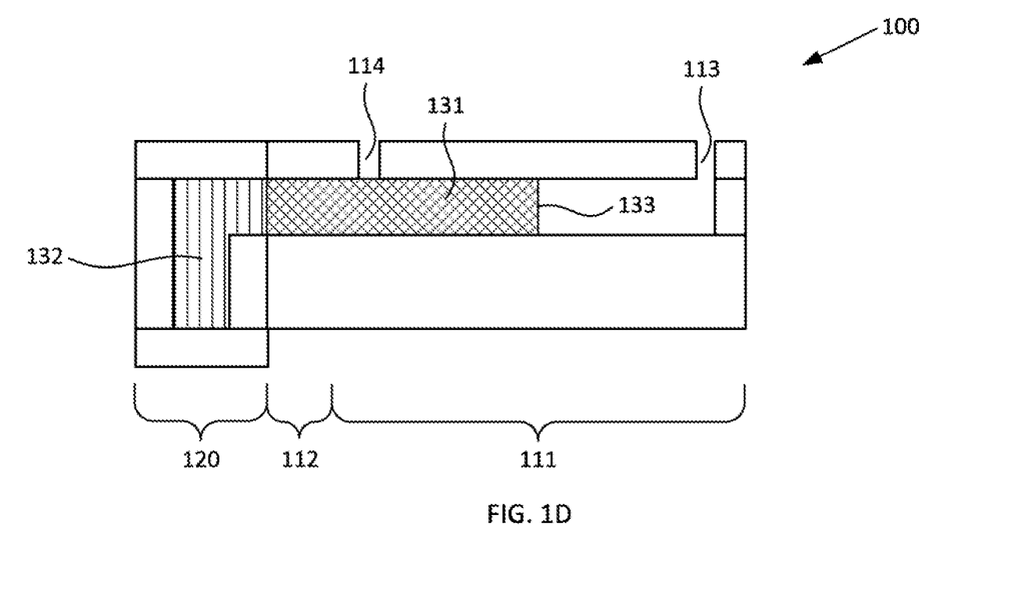

Responsive to centrifugal force applied to device 100, the sample of whole blood disposed within first reservoir 110 separates into a first fraction and a second fraction. For example, FIGS. 1C-1D schematically illustrate a cross-sectional view of the exemplary blood plasma separation device of FIGS. 1A-1B during use, e.g., during operations of the method of FIG. 6 and similarly as illustrated in FIGS. 7A-7B, according to various configurations provided herein. As illustrated in FIG. 1C, first reservoir 110 can receive a sample 130 of whole blood via optional inlet port (aperture) 113. Responsive to centrifugal force in the direction indicated by the large arrow, for example by spinning a disc that includes device 100 in a manner similar to that illustrated in FIG. 5, the sample of whole blood separates into a first fraction 131 and a second fraction 132 in a manner such as schematically illustrated in FIG. 1D. First fraction 131 can be located at least in collection region 111 and can include blood plasma from which substantially all red blood cells have been removed, for example in a manner similar to that described herein with reference to FIG. 7C. Second fraction 132 can be located in second reservoir 120 and can include blood plasma and red blood cells that have been removed from the first fraction by the centrifugal force. As used herein, removal of "substantially all" red blood cells is intended to mean that at least 75% of the red blood cells in the sample of whole blood are removed from the first fraction, or at least 99% of the red blood cells in the sample of whole blood are removed from the first fraction, or 100% of the red blood cells in the sample of whole blood are removed from the first fraction. Such separation of red blood cells (and optionally other types of blood cells) from the blood plasma can be achieved, for example, by applying sufficient centrifugal force to device 100 for a sufficient amount of time. For example, a disc in which device 100 is included can be spun at a rate of 1000 or more revolutions per minute (RPM), a rate of 2000 RPM or more, a rate of 3000 RPM or more, or a rate of 4000 RPM or more, for a sufficient amount of time to remove substantially all red blood cells from the sample of whole blood so as to generate first fraction 131.

In some configurations, responsive to the centrifugal force applied to the device (e.g., via such spinning), optionally a portion of the sample of whole blood 113 contacting the lower surface 118 of collection region 111 flows downward away from cover 116 to contact the lower surface 124 of the second reservoir 120. Optionally, first fraction 131 substantially fills a portion of the first reservoir 110 responsive to the centrifugal force, e.g., substantially fills constricted region 112 and a portion of collection region 111. Additionally, or alternatively, optionally second fraction 132 substantially fills second reservoir 120 responsive to the centrifugal force. As a further or alternative option, first fraction 131 contacts cover 116, and second fraction contacts cover 123, after termination of the centrifugal force. Optionally, first fraction 131 suitably can be removed from first reservoir 110 via any suitable outlet fluidically connected to collection region 111. For example, first fraction 131 can be removed via optional outlet port 114, or via a channel configured similarly to channel 330 described with reference to FIG. 3 which optionally can include an outlet port or can be connected to another device. As yet another option, first fraction 131 can remain within first reservoir 110, e.g., can be optionally analyzed, for example via optical analysis through upper surface 116 and/or lower surface 118 each of which optionally can be at least partially optically transparent.

In various configurations provided herein, constricted region 112 optionally inhibits second fraction 132 from entering collection region 111, e.g., after the centrifugal force is removed. As such, constricted region 112 optionally can inhibit red blood cells (and optionally other types of blood cells) within second fraction from reentering the plasma within first fraction 131, such that substantially all red blood cells continue to be excluded from first fraction 131 even after the centrifugal force is removed.

The constricted region 112 can for venting of air as well as constrict fluid flow to prevent movement of cells after separation. The constricted region 112 can, in some variations, have a cross section with at least one of the dimensions less than 1 mm. The constricted region 112 can have a cross-section that is square, rectangular, and/or circular/semi-circular or any other shape. It is currently 1 mm×0.5 mm but could be other dimensions that similarly constrain flow.

Additionally, or alternatively, in the exemplary configuration illustrated in FIGS. 1A-1D, open area 119 optionally is shallower than, and positioned higher than, open area 125, and as a result blood cells that are forced into second reservoir 120 by centrifugal forces can be inhibited from reentering the plasma of first fraction 131. Optionally, meniscus 133 of first fraction 131 is disposed within collection region 111, e.g., such as illustrated in FIG. 1D. For example, meniscus 133 can extend between the upper and lower surfaces 116, 118 of collection region 111.

Note that first reservoir 110 (and components thereof) and second reservoir 120 (and components thereof) can have any suitable volume, configuration, and dimensions. As one nonlimiting example, first reservoir 110 optionally can have a volume about 25 μL to about 1 mL, or about 50-500 μL, or about 100-250 μL. Additionally, or alternatively, second reservoir 120 optionally can have a volume of about 20-80% of a volume of first reservoir 110, or a volume of about 40-60% of a volume of first reservoir 110. For example, second reservoir 120 optionally can be sized so as to accommodate substantially all of the red blood cells within whole blood sample 130, e.g., following separation of that sample into first and second fractions.

As noted elsewhere herein, first reservoir 110 and second reservoir 120 can have any suitable configuration and include any suitable number of upper surfaces (covers), lower surfaces (covers), and/or sidewalls which respectively can be discrete elements or can be integrally formed with one another. For example, in the nonlimiting example illustrated in FIGS. 1A-1D, optionally the upper surfaces, lower surfaces, and sidewalls can be provided as discrete elements which are suitably coupled to one another. FIGS. 2A-2D schematically illustrate cross-sectional views of alternative blood plasma separation devices, according to various configurations provided herein. Alternative device 200 illustrated in FIG. 2A can include upper surfaces, lower surfaces, and sidewalls which are configured similarly as device 100 described with reference to FIGS. 1A-1D, but in which some of such elements are integrally formed with one another. For example, device 200 can include sidewall element 230 within which respective sidewalls of collection region 211, constricted region 212, and second reservoir 220 can be integrally disposed. Device 200 also can include first cover element 240 within which respective upper surfaces of collection region 211, constricted region 212, and second reservoir 220 can be integrally disposed. Device 200 also can include second cover element 250 within which respective lower surfaces of collection region 211, constricted region 212, and second reservoir 220 can be integrally disposed. Sidewall element 230, first cover element 240, and second cover element 250 can be discrete from one another and suitably coupled to one another.

Figure 2A:
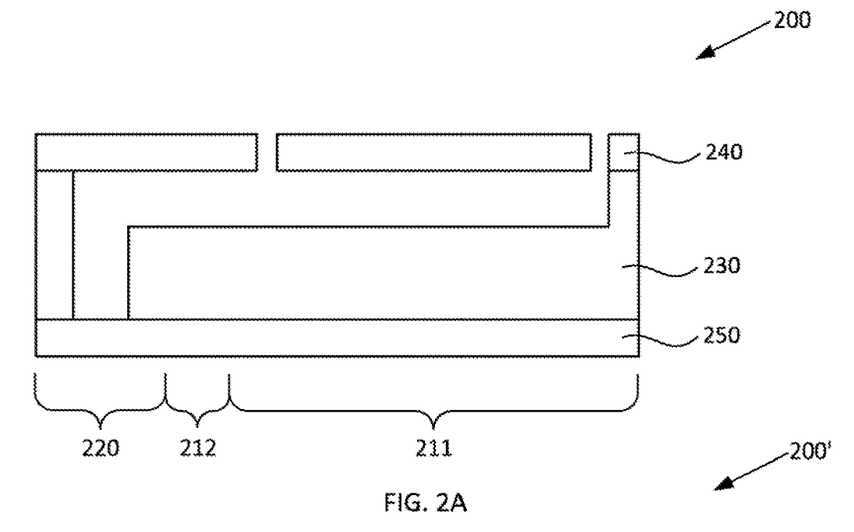
FIGS. 2A-2D schematically illustrate cross-sectional views of alternative blood plasma separation devices, according to various configurations provided herein.
Figure 2B:
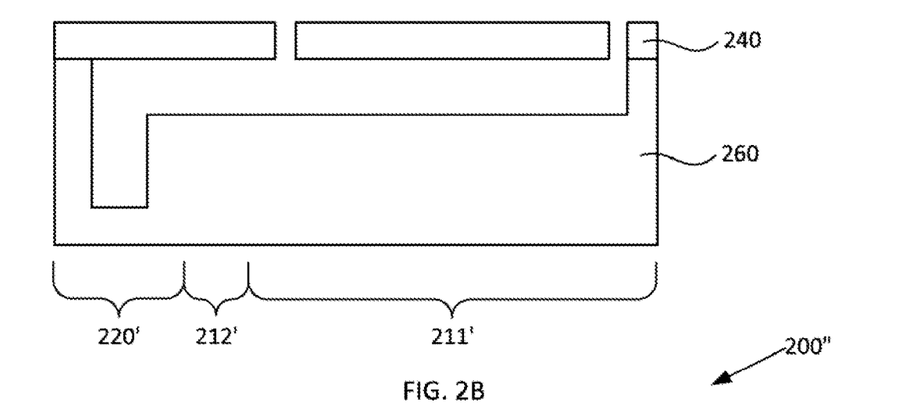

Alternative device 200' illustrated in FIG. 2B can include upper surfaces, lower surfaces, and sidewalls which are configured similarly as device 100 described with reference to FIGS. 1A-1D, but in which some of such elements are integrally formed with one another. For example, device 200' can include combined sidewall/cover element 250 within which respective sidewalls and lower surfaces of collection region 211, constricted region 212, and second reservoir 220 can be integrally disposed. Device 200 also can include cover element 240 within which respective upper surfaces of collection region 211, constricted region 212, and second reservoir 220 can be integrally disposed. Combined sidewall/cover element 250 and cover element 240 can be discrete from one another and suitably coupled to one another.

Figure 2C:
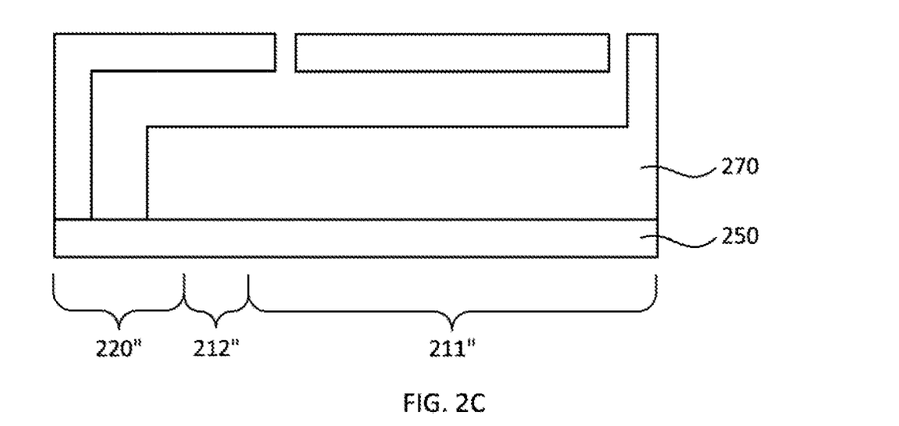

Alternative device 200" illustrated in FIG. 2C can include upper surfaces, lower surfaces, and sidewalls which are configured similarly as device 100 described with reference to FIGS. 1A-1D, but in which some of such elements are integrally formed with one another. For example, device 200" can include combined sidewall/cover element 270 within which respective sidewalls and upper surfaces of collection region 211, constricted region 212, and second reservoir 220 can be integrally disposed. Device 200 also can include cover element 250 within which respective lower surfaces of collection region 211, constricted region 212, and second reservoir 220 can be integrally disposed. Combined sidewall/cover element 270 and cover element 250 can be discrete from one another and suitably coupled to one another.

Figure 2D:
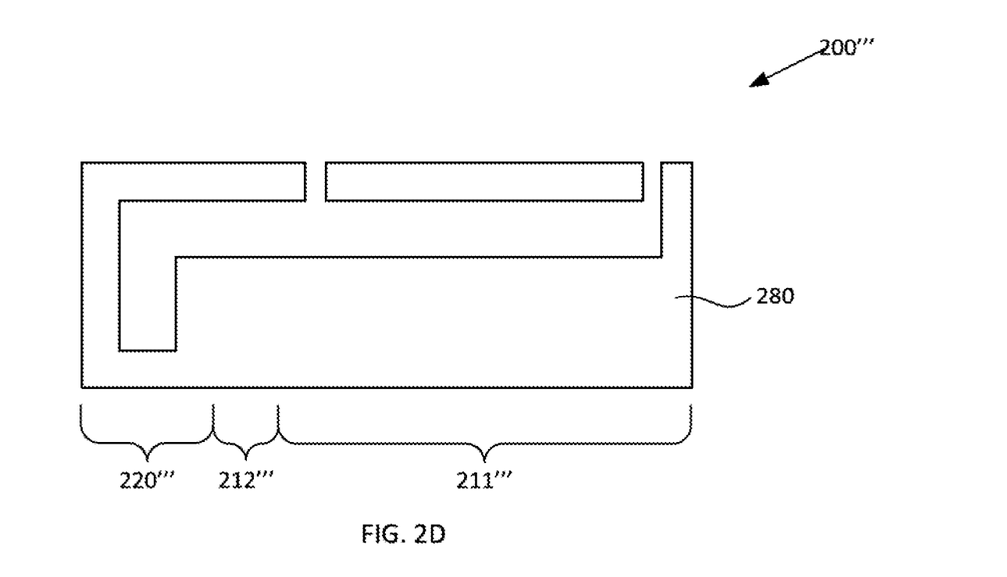

Alternative device 200'" illustrated in FIG. 2D can include upper surfaces, lower surfaces, and sidewalls which are configured similarly as device 100 described with reference to FIGS. 1A-1D, but in which all of such elements are integrally formed with one another. For example, device 200' can include combined sidewall/cover element 280 within which respective sidewalls, upper surfaces, and lower surfaces of collection region 211, constricted region 212, and second reservoir 220 can be integrally disposed.

Figure 3:
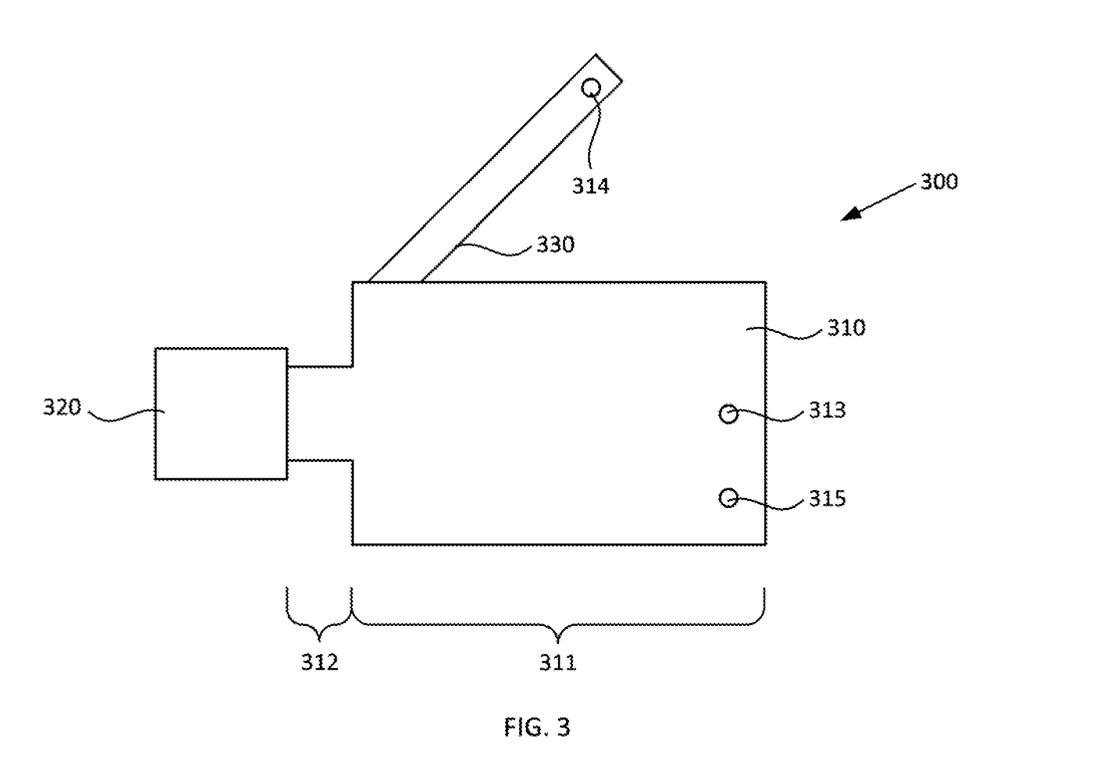
FIG. 3 schematically illustrates a plan view of another alternative blood plasma separation device, according to various configurations provided herein.

As noted elsewhere herein, the first fraction can be removed from the collection region of the first reservoir using any suitable outlet fluidically connected to the collection region, or optionally can be left in place. Optional outlet port 114 illustrated in FIGS. 1A-1D provides one example of such an outlet. Another example is illustrated in FIG. 3, which schematically illustrates a plan view of another alternative blood plasma separation device, according to various configurations provided herein. Device 300 illustrated in FIG. 3 includes first reservoir 310 which can be configured to receive a sample of whole blood comprising red blood cells, and can be configured similarly to first reservoir 110 described with reference to FIGS. 1A-1D. For example, first reservoir 310 optionally can include collection region 311 and constricted region 312. Device 300 further can include second reservoir 320 that is fluidically connected to constricted region 312 of first reservoir 310 and can be configured similarly to second reservoir 120 described with reference to FIGS. 1A-1D. Optionally, device 300 includes inlet 313 via which first reservoir 310 can receive a sample of whole blood in a manner similarly as inlet 113 described with reference to FIGS. 1A-1D, or other suitable structure for introducing a sample of whole blood to first reservoir 310. Additionally, or alternatively, device 300 optionally includes vent 315 via which air can escape from first reservoir 310 when a sample of whole blood is received within that reservoir, e.g., via optional inlet 313.

Device 300 illustrated in FIG. 3 optionally further includes channel 330 which is fluidically connected to the collection region 311. Channel 330 optionally is configured to substantially fill with the first fraction via capillary action responsive to termination of the centrifugal force. In some configurations, optional channel 330 is configured to fluidically connect an outlet 314 to the collection region 311, and the first fraction can be withdrawn from collection region 311 via channel 330 and outlet 314. In other configurations, optional channel 330 is coupled to another device (not specifically illustrated) which can receive the first fraction via the channel. Additionally, or alternatively, channel 330 optionally is disposed at an acute angle relative to the collection region 311, which can inhibit red blood cells from entering the first fraction within the channel.

Figure 4A:
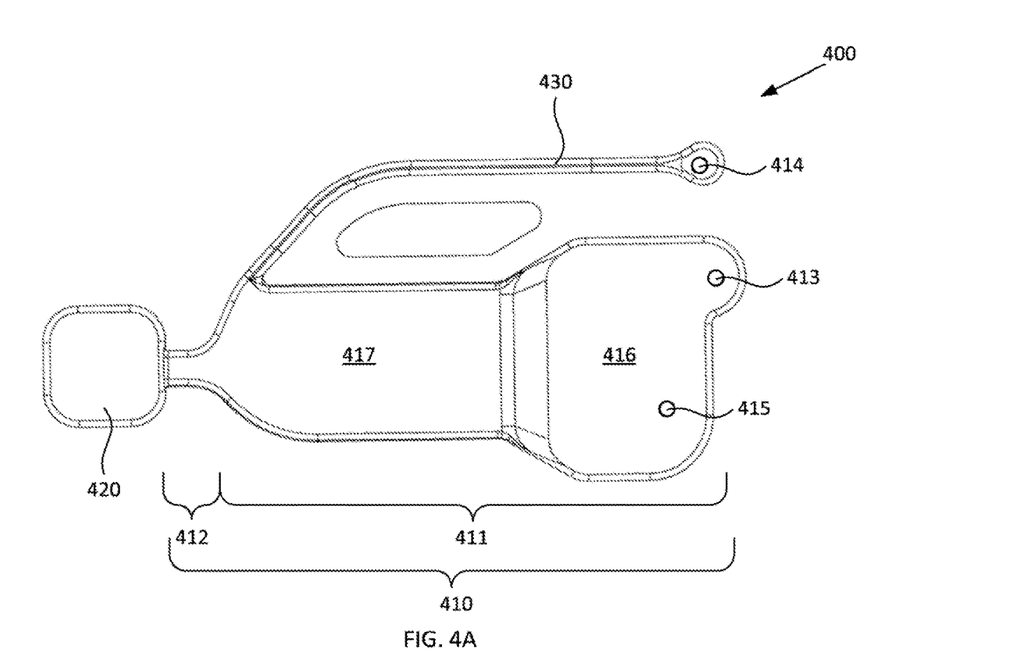
FIGS. 4A-4B schematically illustrate plan and cross-sectional perspective views of components of another alternative blood plasma separation device, according to various configurations provided herein.
Figure 4B:
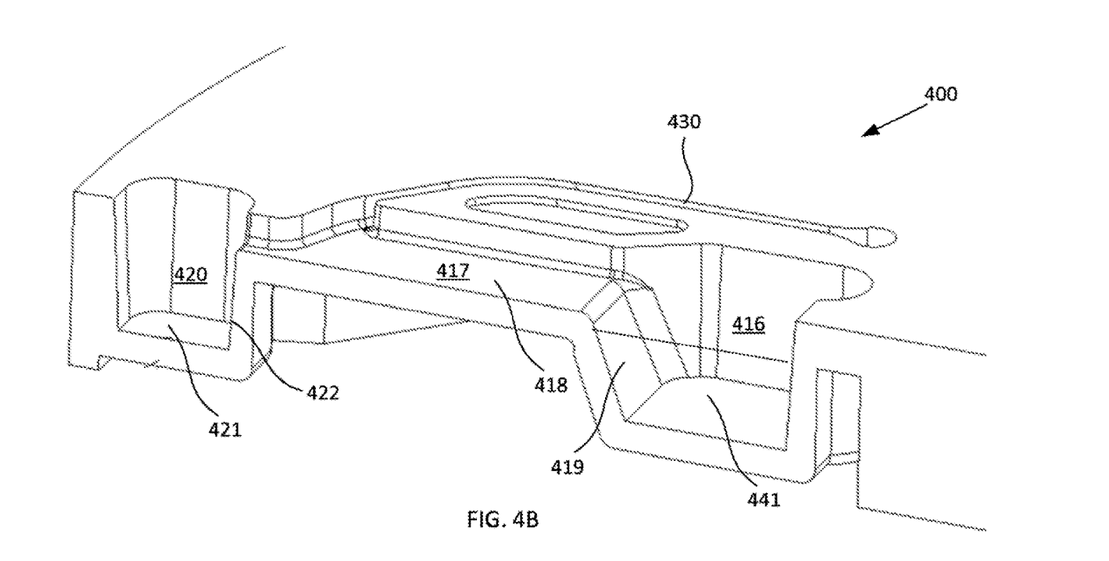

Still other configurations can be envisioned. For example, FIGS. 4A-4B schematically illustrate plan and cross-sectional perspective views of components of another alternative blood plasma separation device, according to various configurations provided herein. In the exemplary configuration illustrated in FIGS. 4A-4B, device 400 includes first reservoir 410, second reservoir 420, and channel 430. First reservoir 410 includes sample reservoir 416 and plasma reservoir 417 which are fluidically connected to one another. Plasma reservoir 417 optionally can include collection region 411 and constricted region 412 which respectively can be configured similarly as collection region 111 and constricted region 112 described with reference to FIGS. 1A-1D. The sample reservoir 416, plasma reservoir 417, and second reservoir 420 each can include one or more respective sidewalls and a respective lower surface, as well as a respective upper surface (omitted in FIG. 4B for clarity), e.g., a cover disposed over the sample reservoir, plasma reservoir, and second reservoir. Any suitable ones of the upper surfaces, lower surfaces, and sidewalls can be discrete from one another or integrally formed with one another, e.g., in a manner similar to that described with reference to FIGS. 2A-2D. For example, in the nonlimiting example shown in FIGS. 4A-4B, the sidewalls and lower surfaces of sample reservoir 416, plasma reservoir 417, and second reservoir 420 can be integrally formed with one another as a single element, and an integrally formed cover suitably can be attached to such element so as to provide upper surfaces of sample reservoir 416, plasma reservoir 417, and second reservoir 420, e.g., in a manner similar to that described with reference to FIG. 2B. Optionally, sample reservoir 416, plasma reservoir 417, and second reservoir 420 are arranged linearly with one another, e.g., such as illustrated in FIGS. 4A-4B.

The cover of device 400, which can form the upper surfaces of the first and second reservoirs 410, 420, optionally can include first aperture (inlet port) 413 via which sample reservoir 416 can receive the sample of whole blood, and/or second aperture 414 (outlet port) via which the first fraction can be withdrawn. First aperture 413 optionally can be disposed over sample reservoir 416 and configured similarly as first aperture (inlet port) 113 described with reference to FIGS. 1A-1D. Optionally, second aperture 414 can be disposed over the plasma reservoir 417 and configured similarly as second aperture 413 described with reference to FIGS. 1A-1D. Alternatively, in the exemplary configuration illustrated in FIG. 4A, device 400 optionally includes channel 430 which is fluidically connected to the collection region 411, for example to plasma reservoir 417. Channel 430 optionally is configured to substantially fill with the first fraction via capillary action responsive to termination of the centrifugal force. In some configurations, optional channel 430 is configured to fluidically connect outlet 414 to the collection region 411, and the first fraction can be withdrawn from collection region 411 via channel 430 and outlet 414. In other configurations, optional channel 430 is coupled to another device (not specifically illustrated) which can receive the first fraction via the channel. Additionally, or alternatively, channel 430 optionally is disposed at an acute angle relative to the collection region 411, which can inhibit red blood cells from entering the first fraction within the channel. If present, each of first aperture 413 and second aperture 414 independently optionally can be configured to receive a pipette tip. Additionally, or alternatively, the cover of device 400 optionally includes vent 415 disposed over sample reservoir 416 so as to provide an outlet for air that is displaced when depositing a sample of whole blood into sample reservoir 416. Additionally, or alternatively, the cover of device 400 optionally can be at least partially optically transparent, for example to facilitate visual or optical analysis of the blood sample or fractions within the device.

In the exemplary configuration illustrated in FIGS. 4A-4B, the respective lower surface 418 of the plasma reservoir 417 optionally is closer to the cover (not shown in FIG. 4B, but generally extending in a plane immediately above first and second reservoirs 410, 420) than are the respective lower surfaces 441, 421 of the sample reservoir 416 and second reservoir 420. Optionally, an upper surface (exemplary level indicated with dotted lines in FIG. 4B) of the sample of whole blood disposed within the sample reservoir 420 is further from the cover than is the lower surface 418 of plasma reservoir 417. As such, when the sample of whole blood initially is deposited within sample chamber 416, the sample remains within that chamber under the force of gravity until centrifugal force is applied. Then, responsive to the centrifugal force applied to device 400, the sample of whole blood disposed within sample reservoir 416 flows upward toward the cover to contact lower surface 418 of plasma reservoir 417. For example, optionally a first one of the sidewalls 419 of sample reservoir 416 can be disposed at an obtuse angle relative to lower surface 441 of the sample reservoir. Responsive to the centrifugal force applied to device 400, substantially all of the sample of whole blood disposed within sample reservoir 416 flows upward along sidewall 419 of the sample reservoir, e.g., to contact lower surface 418 of plasma reservoir 417. As a further option, responsive to the centrifugal force applied to device 400, a portion of the sample of whole blood contacting the lower surface 418 of plasma reservoir 417 flows downward away from the cover to contact lower surface 421 of second reservoir 420. For example, responsive to the centrifugal force applied to device 400, the portion of the sample of whole blood contacting lower surface 418 of plasma reservoir 417 flows downward along a first one of the sidewalls 422 of second reservoir 420.

In a manner similar to that described with reference to FIGS. 1A-1D, in some configurations the first and second fractions each contact the cover of device 400 after termination of the centrifugal force. Additionally, or alternatively, optionally the first fraction can substantially fill plasma reservoir 417 responsive to the centrifugal force, e.g., in a manner similar to that described with reference to FIGS. 1A-1D. Additionally, or alternatively, optionally the second fraction substantially fills second reservoir 420 responsive to the centrifugal force, e.g., in a manner similar to that described with reference to FIGS. 1A-1D. Additionally, or alternatively, optionally a meniscus of the first fraction is disposed within the collection region, e.g., in a manner similar to that described with reference to FIGS. 1A-1D. For example, meniscus 133 can extend between the upper and lower surfaces of collection region 411, e.g., within plasma reservoir 417 in a manner similar to that described with reference to FIG. 1D.

Figure 5:
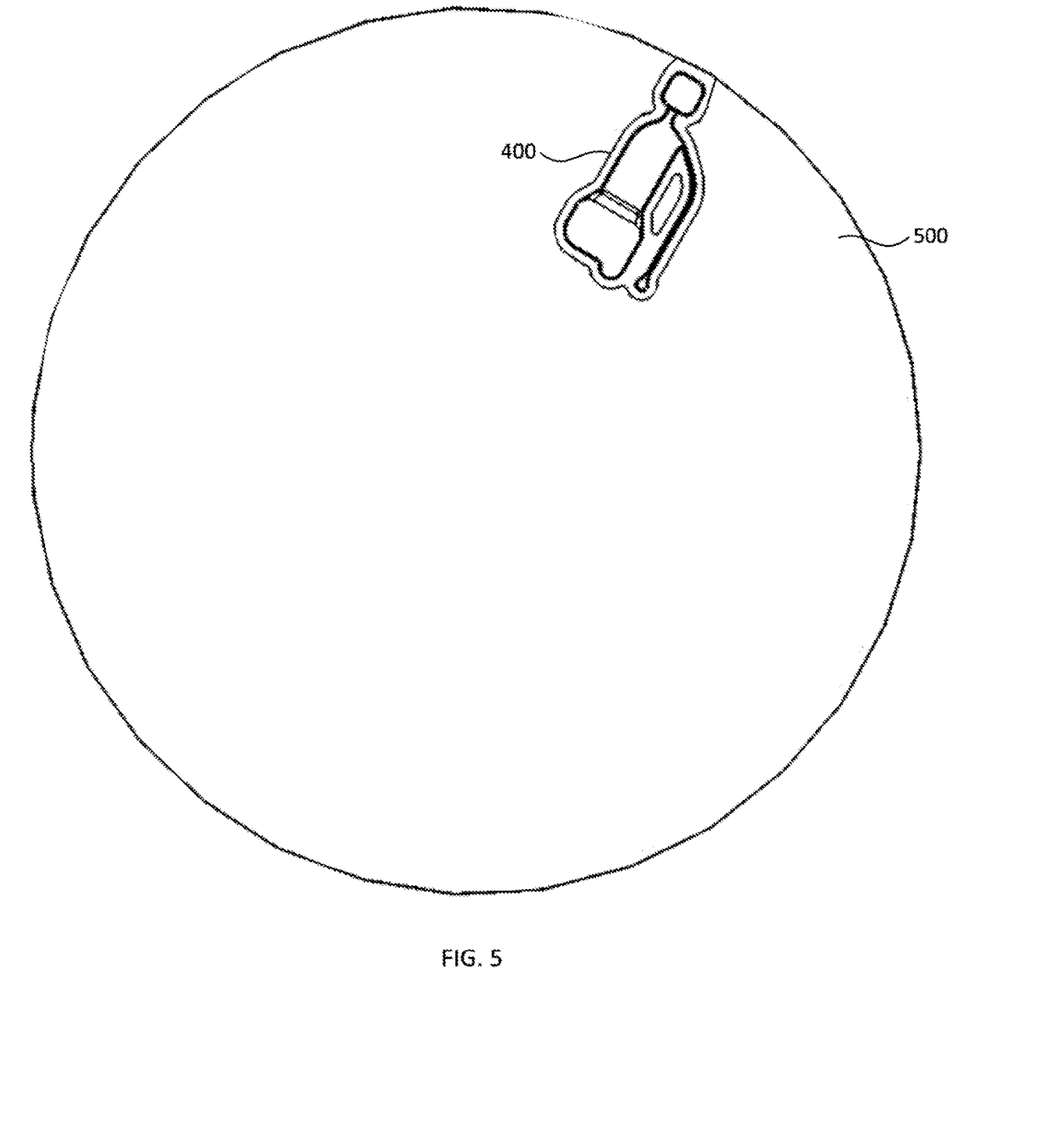
FIG. 5 schematically illustrates a plan view of a disc including the device of FIGS. 4A-4B, according to various configurations provided herein.

As noted elsewhere herein, centrifugal force can be applied to the present devices so as to separate a sample of whole blood into the first and second fractions. For example, FIG. 5 schematically illustrates a plan view of a disc including the device 400 of FIGS. 4A-4B, according to various configurations provided herein. The rotatable disc in which first and second reservoirs are disposed, can be spun at any suitable rate, and for any suitable amount of time, so as to generate the first and second fractions in a manner such as exemplified herein. Note that although disc 500 specifically illustrated in FIG. 5 includes the device 400 of FIGS. 4A-4B, disc 500 instead can include any other device provided herein, such as any of devices 100, 200, 200', 200", 200''', 300, or 400.

Figure 6:
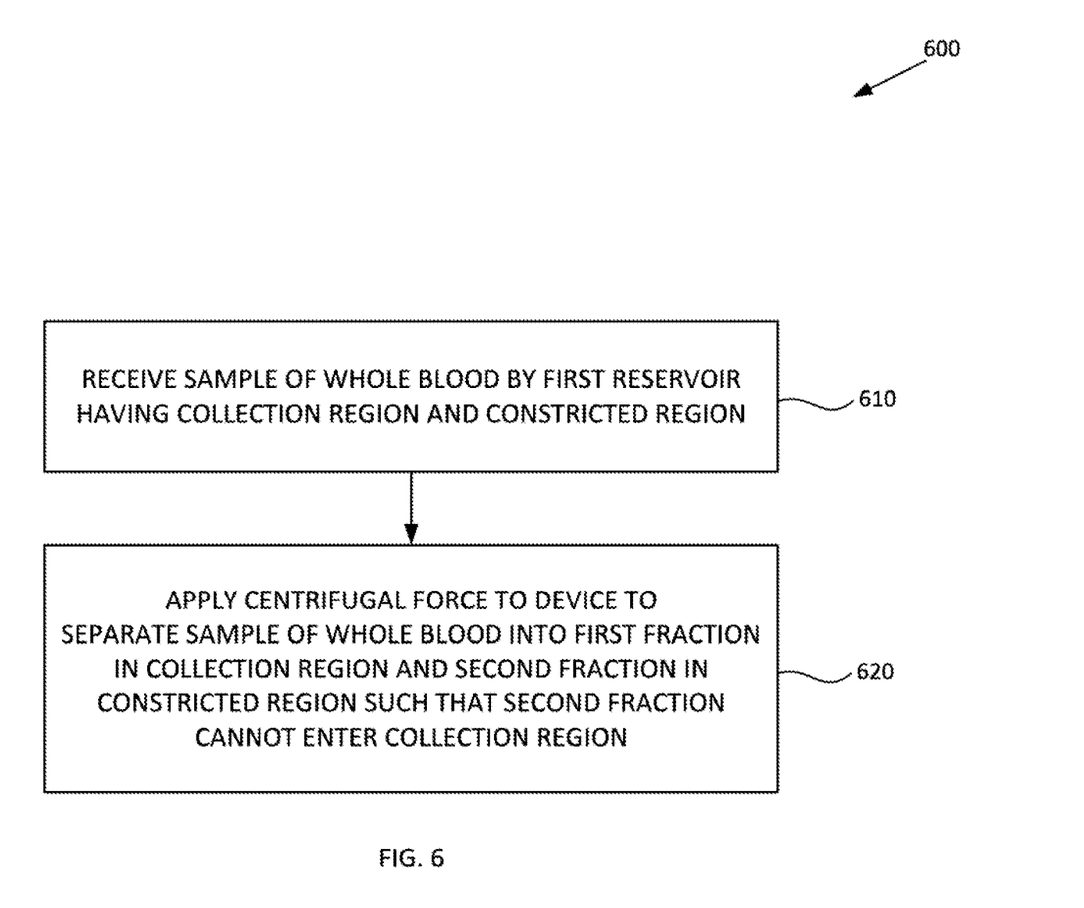
FIG. 6 illustrates an exemplary flow of operations in a method of using the devices of FIGS. 1A-5, according to various configurations provided herein.
Figure 7A:
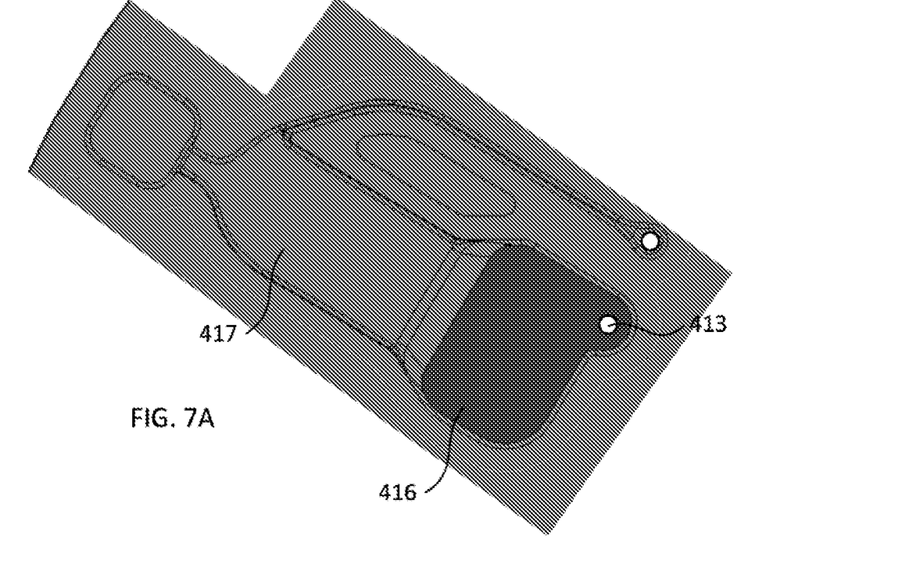
FIGS. 7A-7D schematically illustrate plan views of components of a blood plasma separation device during operations of the method of FIG. 6, according to various configurations provided herein.
Figure 7B:
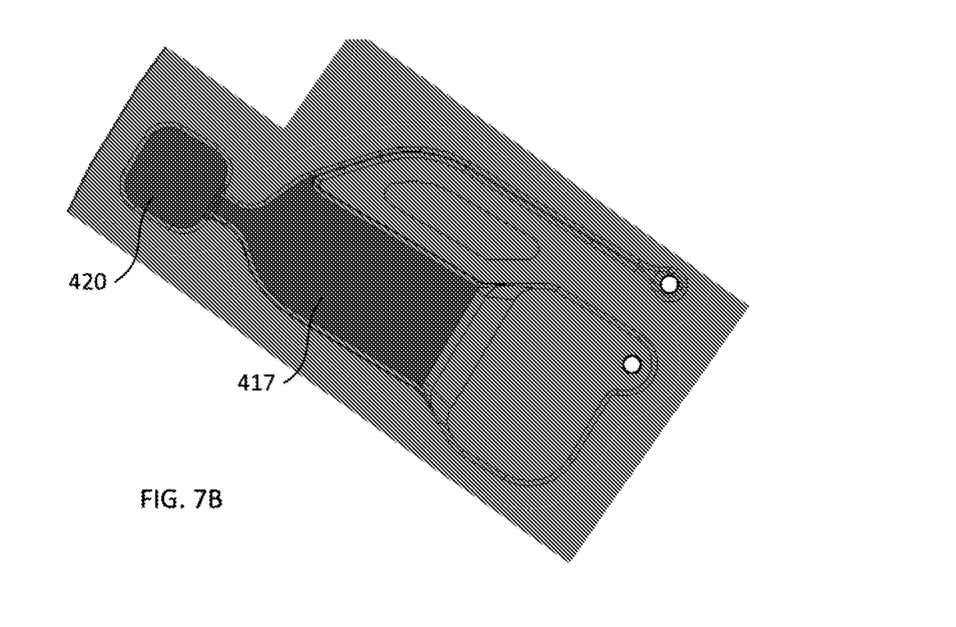

FIG. 6 illustrates an exemplary flow of operations in a method of using the devices of FIGS. 1A-5, and FIGS. 7A-7D schematically illustrate plan views of components of a blood plasma separation device during operations of the method of FIG. 6, according to various configurations provided herein. Method 600 illustrated in FIG. 6 can include receiving, by a first reservoir of a device, a sample of whole blood comprising red blood cells (610). The first reservoir can include a collection region and a constricted region, e.g., in a manner such as described with reference to the first reservoirs of any of devices 100, 200, 200', 200", 200''', 300, or 400. For example, in the nonlimiting example illustrated in FIG. 7A, the first reservoir can include sample reservoir 416 and plasma reservoir 417 fluidically connected to one another, wherein sample reservoir 416 includes inlet 413 configured to receive the sample of whole blood and plasma reservoir 417 includes the collection region and the constricted region. Sample chamber 416 can be filled with a sample of whole blood through optional inlet port 413 or other suitable structure.

Method 600 illustrated in FIG. 6 can include applying a centrifugal force to the device to separate the sample of whole blood into a first fraction and a second fraction (620). The first fraction can be located in the collection region and including blood plasma from which substantially all red blood cells have been removed. The second fraction can be located in a second reservoir of the device and comprising blood plasma and red blood cells that have been removed from the first fraction by the centrifugal force. The constricted region can inhibit the second fraction from entering the collection region. For example, in the nonlimiting example illustrated in FIG. 7B, as a disc or other structure including the device (e.g., disc 500) begins to spin to generate centrifugal force, the sample of whole blood migrates to substantially fill second reservoir 420 and plasma reservoir 417. For example, responsive to the centrifugal force, the sample of whole blood disposed within sample reservoir 416 flows upward toward the cover to contact lower surface 418 of plasma reservoir 417. Illustratively, in a manner such as described with reference to FIGS. 4A-4B, a first one of the sidewalls 419 of sample reservoir 416 can be disposed at an obtuse angle relative to the lower surface of the sample reservoir, and responsive to the centrifugal force applied to the device, substantially all of the sample of whole blood disposed within sample reservoir 416 flows upward along the first one of the sidewalls 419 of sample reservoir 416. Further, in a manner such as described with reference to FIGS. 4A-4B, optionally responsive to the centrifugal force applied to the device, a portion of the sample of whole blood contacting lower surface 418 of plasma reservoir 417 flows downward away from the cover to contact lower surface 421 of second reservoir 420, e.g., downward along a first one of the sidewalls 422 of the second reservoir.

Figure 7C:
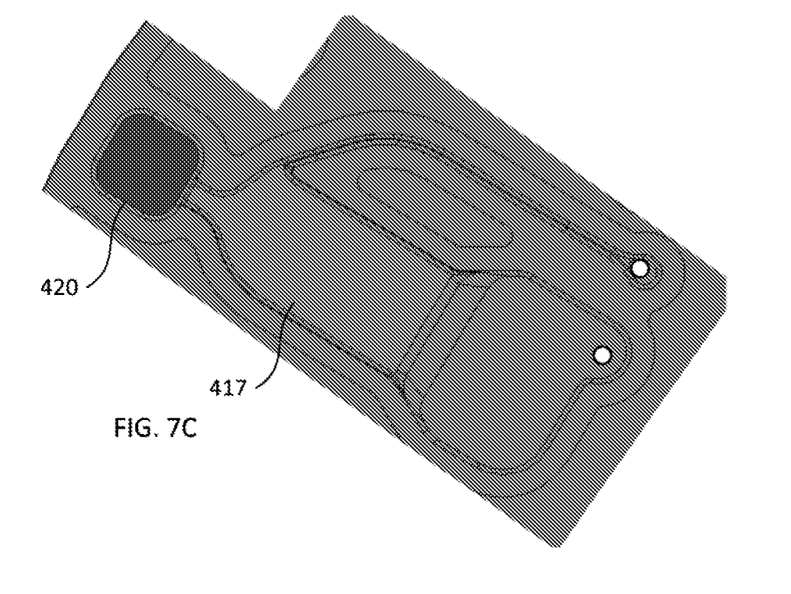

After continuing to spin the disc or other structure including the device at a suitable rate and for a suitable amount of time, substantially all red blood cells within the sample of whole blood form a pellet in second reservoir 420 to form a second fraction, and blood plasma from which substantially all red blood cells have been removed forms a first fraction that substantially fills plasma reservoir 417, such as illustrated in FIG. 7C. For example, the first fraction optionally substantially fills plasma reservoir 417 responsive to the centrifugal force, and/or the second fraction substantially fills second reservoir 420 responsive to the centrifugal force. At least 75%, at least 99%, or even 100% of the red blood cells in the sample of whole blood optionally can be removed from the first fraction.

Figure 7D:
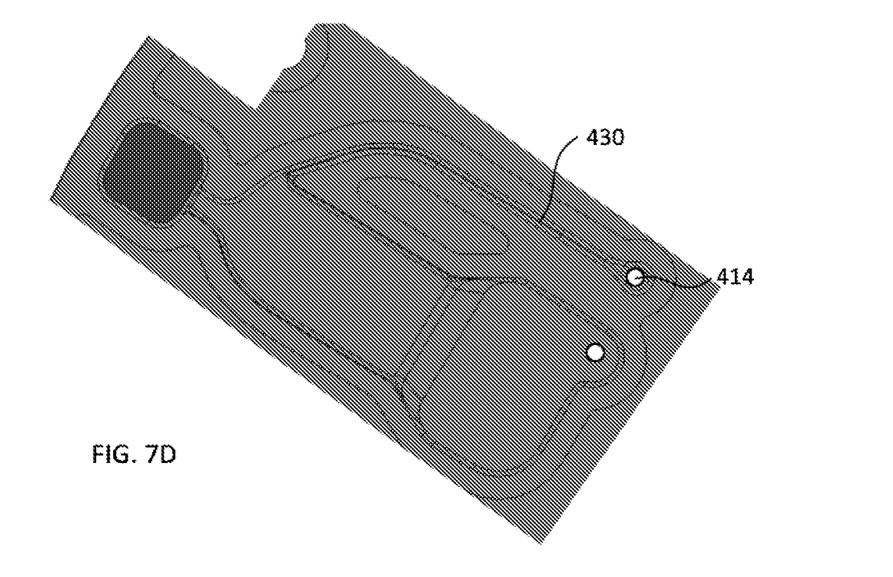

Method 600 illustrated in FIG. 6 optionally includes removing the first fraction from the collection region. For example, optionally an outlet fluidically connects to the collection region (e.g., to plasma reservoir 417), such as outlet port (aperture) 414 illustrated in FIGS. 4A-4B and 7D, or outlet port 114 illustrated in FIGS. 1A-1D, or outlet port 314 illustrated in FIG. 3. As a further option, a channel fluidically connects the outlet to the collection region, such as channel 330 illustrated in FIG. 3 or channel 414 illustrated in FIGS. 4A-4B and 7D. In a manner such as described elsewhere herein, the channel optionally can be disposed at an acute angle relative to the collection region. As illustrated in FIG. 7D, the channel optionally substantially fills with the first fraction via capillary action responsive to termination of the centrifugal force. Additionally, or alternatively, the first and second fractions each optionally can contact the cover of the device after termination of the centrifugal force.

In some configurations, the present devices and methods are based on centrifugal separation of whole blood into red blood cell and plasma components, which respectively can be referred to herein as second and first fractions. The present devices optionally can sit radially on a disc, e.g., such as illustrated in FIG. 5, in which whole blood can be loaded through an inlet port (fill hole) into a first reservoir, such as a sample reservoir (fill chamber) which can be closer to the center of the disc than are other components of the present devices. In one nonlimiting example, the sample reservoir includes a 5 mm deep area designed to hold sufficient volume based on a 110 µL sample size, for example to inhibit or prevent spillage of the blood either into the optional outlet channel during fill, or into the fill and outlet holds during spin start. As the disc is accelerated, blood transfers towards the outside (circumference) of the disc, filling the second reservoir which in one nonlimiting example includes a 5 mm deep chamber at the bottom of the design, as well as the plasma reservoir/collection region which in one nonlimiting example is in the middle of the design. The relatively low depth (shallowness) of the plasma reservoir can inhibit or prevent collapse of the plasma-air interface after spinning has stopped, such that a meniscus of the plasma can remain within the plasma reservoir in a manner similar to that illustrated in FIG. 1D. As spinning continues, plasma and red blood cells separate based on centrifugal forces. Optionally, the second reservoir can be designed such that it can contain more than about 60.9% volume of a 110 µL loaded blood. The 60.9% hematocrit level ("worst case hematocrit") represents average hematocrit plus 3 standard deviations, which should account for 99.7% of the population. Therefore, in some configurations substantially all of the red blood cells become disposed in the second reservoir as a result of the centrifugal forces, and blood plasma from which substantially all of the red blood cells have been removed becomes disposed in the collection region of the first reservoir (plasma reservoir). As the disc stops spinning, plasma gets drawn into an outlet channel (which can have an exemplary cross-sectional area of about 0.5 mm by 0.5 mm) via capillary force, thus allowing for an air-free aspiration of plasma from an outlet port coupled to, e.g., positioned above, the outlet channel. In some configurations, the only vent during aspiration of the plasma is the inlet port, allowing fluid to be collected until air connects the inlet and outlet ports to one another within the device (referred to as airknifing). Such airknifing together with the constriction region can stabilize the red blood cells within the second reservoir and allow retrieval of substantially only the first fraction without reintroduction of red blood cells from the second fraction.

The present devices can be constructed using any suitable materials or combination of materials, such as any suitable combination of polymer, glass, metal, and semiconductor. Additionally, the present devices can be constructed using any suitable fabrication technique(s), such as molding, 3D printing, machining, using laminate assemblies, thermoforming, chemical or laser etching, casting, and/or hot embossing.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it is used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." In addition, use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method for separating blood plasma from whole blood, the method comprising: receiving, by a first reservoir of a device, a sample of whole blood comprising red blood cells, the first reservoir comprising:
a collection region;
a channel fluidly connecting the collection region to an outlet; and
a constricted region; and
applying a centrifugal force to the device to separate the sample of whole blood into a first fraction and a second fraction,
the first fraction being located in the collection region and comprising blood plasma from which substantially all red blood cells have been removed,
the second fraction being located in a second reservoir of the device and
comprising blood plasma and red blood cells that have been removed from the first fraction by the centrifugal force,
the channel substantially being filled with the first fraction via capillary action responsive to termination of the centrifugal force, and
the constricted region inhibits the second fraction from entering the collection region.

2. The method of claim 1, wherein the channel is disposed at an acute angle relative to the collection region.

3. The method of claim 1, wherein the first reservoir comprises a sample reservoir and a plasma reservoir fluidically connected to one another,
the sample reservoir comprising an inlet configured to receive the sample of whole blood, the plasma reservoir comprising the collection region and the constricted region.

4. The method of claim 3, wherein the sample reservoir, plasma reservoir, and second reservoir each comprises one or more respective sidewalls and a respective lower surface.

5. The method of claim 3, wherein a cover is disposed over the sample reservoir, plasma reservoir, and second reservoir.

6. The method of claim 5, wherein the respective lower surface of the plasma reservoir is closer to the cover than are the respective lower surfaces of the sample reservoir and the second reservoir.

7. The method of claim 6, wherein an upper surface of the sample of whole blood disposed within the sample reservoir is further from the cover than is the lower surface of the plasma reservoir.

8. The method of claim 7, wherein responsive to the centrifugal force applied to the method, the sample of whole blood disposed within the sample reservoir flows upward toward the cover to contact the lower surface of the plasma reservoir.

9. The method of claim 8, wherein:
a first one of the sidewalls of the sample reservoir is disposed at an obtuse angle relative to the lower surface of the sample reservoir, and
responsive to the centrifugal force applied to the device, substantially all of the sample of whole blood disposed within the sample reservoir flows upward along the first one of the sidewalls of the sample reservoir.

10. The method of claim 8, wherein responsive to the centrifugal force applied to the device, a portion of the sample of whole blood contacting the lower surface of the plasma reservoir flows downward away from the cover to contact the lower surface of the second reservoir.

11. The method of claim 10, wherein responsive to the centrifugal force applied to the device, the portion of the sample of whole blood contacting the lower surface of the plasma reservoir flows downward along a first one of the sidewalls of the second reservoir.

12. The method of claim 5, wherein the first and second fractions each contact the cover after termination of the centrifugal force.

13. The method of claim 5, wherein the cover is at least partially optically transparent.

14. The method of claim 5, wherein the cover comprises:
a first aperture via which the sample reservoir receives the sample of whole blood; and
a second aperture via which the first fraction is withdrawn.

15. The method of claim 14, wherein the first aperture is disposed over the sample reservoir.

16. The method of claim 15, wherein the second aperture is disposed over the plasma reservoir.

17. The method of claim 15, wherein the second aperture is located over the channel.

18. The method of claim 14, wherein the first and second apertures each are configured to receive a pipette tip.

19. The method of claim 5, wherein the cover further comprises a vent disposed over the sample reservoir.

20. The method of claim 3, wherein the second fraction substantially fills the second reservoir responsive to the centrifugal force.

21. The method of claim 3, wherein the sample reservoir, the plasma reservoir, and the second reservoir are arranged linearly with one another.

22. The method of claim 3, wherein a meniscus of the first fraction is disposed within the collection region.

23. The method of claim 1, wherein the first fraction substantially fills the plasma reservoir responsive to the centrifugal force.

24. The method of claim 1, wherein at least 75% of the red blood cells in the sample of whole blood are removed from the first fraction.

25. The method of claim 1, wherein at least 99% of the red blood cells in the sample of whole blood are removed from the first fraction.

26. The method of claim 1, wherein 100% of the red blood cells in the sample of whole blood are removed from the first fraction.

27. The method of claim 1, wherein the first reservoir has a volume about 25 µL to about 1 mL, or about 50-500 or about 100-250 µL.

28. The method of claim 1, wherein the second reservoir has a volume of about 20-80% of a volume of the first reservoir, or a volume of about 40-60% of a volume of the first reservoir.

29. The method of claim 1, wherein the first and second reservoirs are disposed in a rotatable disc.

* * * * *